(12) United States Patent
Watanabe et al.

(10) Patent No.: US 11,457,666 B2
(45) Date of Patent: Oct. 4, 2022

(54) CARTRIDGE HAVING PARTITION MEMBER AND HEATER AND INHALER INCLUDING SAME

(71) Applicant: JAPAN TOBACCO INC., Tokyo (JP)

(72) Inventors: Tomoichi Watanabe, Tokyo (JP); Hirofumi Matsumoto, Tokyo (JP); Takuma Nakano, Tokyo (JP); Kei Oishi, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 544 days.

(21) Appl. No.: 16/518,393

(22) Filed: Jul. 22, 2019

(65) Prior Publication Data

US 2019/0343186 A1 Nov. 14, 2019

Related U.S. Application Data

(63) Continuation of application No. PCT/JP2017/004490, filed on Feb. 8, 2017.

(51) Int. Cl.
*A24F 13/00* (2006.01)
*A24F 17/00* (2006.01)
(Continued)

(52) U.S. Cl.
CPC ............ *A24F 40/485* (2020.01); *A24F 40/42* (2020.01); *A24B 15/167* (2016.11); *A24F 40/10* (2020.01); *A61M 2205/8206* (2013.01)

(58) Field of Classification Search
CPC ........ A24F 40/10; A24F 40/42; A24F 40/485; A24B 15/167; A61M 2205/8206
See application file for complete search history.

(56) References Cited

U.S. PATENT DOCUMENTS 5,894,841 A 4/1999 Voges
9,078,475 B2 * 7/2015 Li .................. A61M 11/042
(Continued)

FOREIGN PATENT DOCUMENTS

CN 3560360 * 12/2016 ........... A24F 47/008
EP 2 941 969 A1 11/2015
(Continued)

OTHER PUBLICATIONS

Japanese Office Action for Japanese Application No. 2018-566683, dated Aug. 27, 2020, with English translation.
(Continued)

*Primary Examiner* — Abdullah A Riyami
*Assistant Examiner* — Thang H Nguyen
(74) *Attorney, Agent, or Firm* — Birch, Stewart, Kolasch & Birch, LLP

(57) ABSTRACT

To provide an inhaler cartridge and an inhaler including a novel structure.
Provided is a cartridge for an inhaler. The cartridge includes: a housing including an accommodation space capable of accommodating a liquid, an air flow passage, and a partition member partitioning the accommodation space and the air flow passage in a longitudinal direction; and a heater configured to be capable of heating the liquid and arranged in the air flow passage. The partition member includes an opening opened in a transverse direction to bring the accommodation space into communication with the air flow passage. The opening includes an upstream-side opening edge and a downstream-side opening edge. The partition member includes an upstream-side end and a downstream-side end. A distance between the upstream-side opening edge and the upstream-side end is smaller than a distance between the downstream-side opening edge and the downstream-side end.

6 Claims, 13 Drawing Sheets

(51) Int. Cl.
　　　*A24F 25/00*　　　(2006.01)
　　　*A24F 40/485*　　(2020.01)
　　　*A24F 40/42*　　　(2020.01)
　　　*A24B 15/167*　　(2020.01)
　　　*A24F 40/10*　　　(2020.01)

(56) References Cited

U.S. PATENT DOCUMENTS

| | | | | |
|---|---|---|---|---|
| 9,497,996 | B2 * | 11/2016 | Liu | A61M 15/06 |
| 2013/0192623 | A1 * | 8/2013 | Tucker | H05B 3/10 |
| | | | | 131/329 |
| 2014/0360516 | A1 | 12/2014 | Liu | |
| 2015/0237913 | A1 | 8/2015 | Suzuki et al. | |
| 2016/0128384 | A1 * | 5/2016 | Luciani | B65D 1/08 |
| | | | | 215/44 |
| 2018/0169357 | A1 * | 6/2018 | Reevell | A61M 11/042 |
| 2018/0242642 | A1 * | 8/2018 | Silvesstrini | H05B 3/03 |
| 2019/0297952 | A1 * | 10/2019 | Qiu | A24F 40/48 |

FOREIGN PATENT DOCUMENTS

| | | |
|---|---|---|
| GB | 2494315 A | 3/2013 |
| JP | 8-511966 A | 12/1996 |
| JP | 2015-506182 A | 3/2015 |
| JP | 5895062 B2 | 3/2016 |
| JP | 2016-521981 A | 7/2016 |
| WO | WO 2013/116672 A1 | 8/2013 |
| WO | WO 2016/096780 A1 | 6/2016 |

OTHER PUBLICATIONS

Extended European Search Report for European Application No. 17895817.9, dated Nov. 13, 2020.
International Search Report (PCT/ISA/210) issued in PCT/JP2017/004490, dated Mar. 21, 2017.
Korean Office Action for Korean Application No. 10-2019-7023183, dated Jan. 26, 2021, with English translation.

* cited by examiner

CARTRIDGE HAVING PARTITION MEMBER AND HEATER AND INHALER INCLUDING SAME

CROSS REFERENCE TO RELATED APPLICATIONS

The present application is a continuation application of International Application No. PCT/JP2017/004490, filed on Feb. 8, 2017.

TECHNICAL FIELD

The present invention relates to a cartridge and an inhaler.

BACKGROUND ART

Flavor inhalers for inhaling flavor without burning a material have been known. As such flavor inhalers, for example, electronic cigarettes are known. Electronic cigarettes supply an aerosol generated by atomizing a liquid containing a flavor such as nicotine (equivalent to an example of an aerosol source) to the user's mouth, or cause an aerosol generated by atomizing a liquid that does not contain a flavor such as nicotine (equivalent to an example of an aerosol source) to pass through a flavor source (e.g., a tobacco source) and then supply the aerosol to the user's mouth.

Some electronic cigarettes include a tank or reservoir that accommodates a liquid for generating an aerosol, and a heater that atomizing the liquid. Some such electronic cigarettes include an insulating ring for mutually insulating a pair of conducting wires connecting the heater and the battery (see, for example, PTL 1).

CITATION LIST

Patent Literature

PTL 1: EP Patent Application Publication No. 2941969

SUMMARY OF INVENTION

Technical Problem

It is an object of the present invention to provide an inhaler cartridge and an inhaler with a novel structure.

Solution to Problem

According to an aspect of the present invention, there is provided a cartridge for an inhaler. The cartridge includes: a housing including an accommodation space capable of accommodating a liquid, an air flow passage, and a partition member partitioning the accommodation space and the air flow passage in a longitudinal direction; and a heater configured to be capable of heating the liquid and arranged in the air flow passage. The partition member includes an opening opened in a transverse direction to bring the accommodation space into communication with the air flow passage. The opening includes an upstream-side opening edge and a downstream-side opening edge. The partition member includes an upstream-side end and a downstream-side end. A distance between the upstream-side opening edge and the upstream-side end is smaller than a distance between the downstream-side opening edge and the downstream-side end.

According to an aspect of the present invention, the partition member includes an upstream portion positioned between the upstream-side opening edge and the upstream-side end and a downstream portion positioned between the downstream-side end and the downstream-side end, and a longitudinal length of the downstream portion is longer than a longitudinal length of the upstream portion.

According to an aspect of the present invention, the heater includes an upstream-side heater end and a downstream-side heater end, and a distance between the upstream-side heater end and the upstream-side end is smaller than a distance between the downstream-side heater end and the downstream-side end.

According to an aspect of the present invention, the cartridge includes a liquid holding member arranged to cover the liquid supply port, in which the liquid holding member is arranged between the liquid supply port and the heater.

According to an aspect of the present invention, the housing includes an air outlet port communicating with the air flow passage.

According to an aspect of the present invention, the cartridge includes an air inlet port provided at a position facing the heater and communicating with the air flow passage.

According to an aspect of the present invention, there is provided an inhaler. The inhaler includes: the cartridge; and a battery portion configured to supply electric power to the heater of the cartridge.

DESCRIPTION OF EMBODIMENTS

First Embodiment

Figure 1:
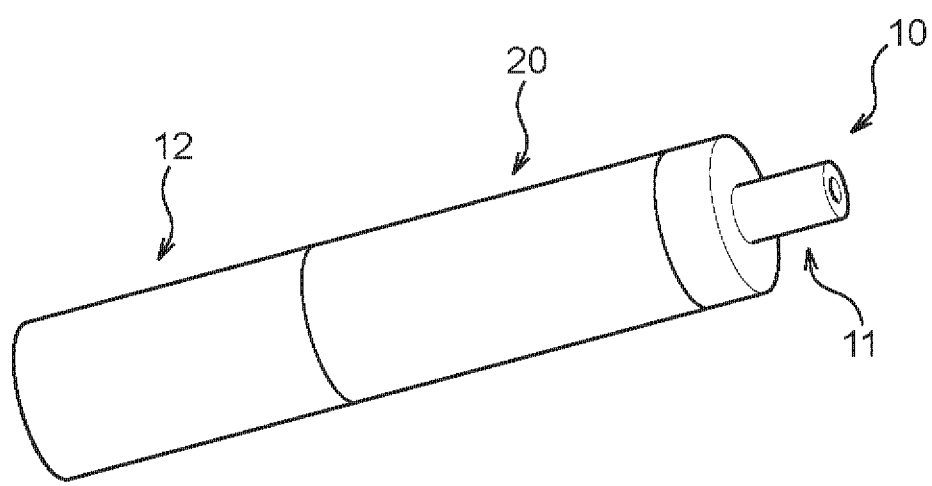
FIG. 1 is an overall perspective view of an inhaler according to a first embodiment.

A first embodiment of the present invention is described below with reference to the drawings. In the drawings described below, the same or equivalent constituent elements are designated with the same reference numerals, and a repetitive description will be omitted.

FIG. 1 is an overall perspective view of an inhaler according to the first embodiment. As illustrated in FIG. 1, an inhaler 10 includes a mouthpiece 11, a cartridge 20, and a battery portion 12. The cartridge 20 atomizes a liquid including a flavor containing a component, e.g., nicotine, and supplies the aerosol toward the mouthpiece 11. The battery portion 12 supplies electric power to the cartridge 20. The mouthpiece 11 guides the aerosol generated in the cartridge 20 to the user's mouth. After the inhaler 10 is used over a predetermined period of time, the mouthpiece 11 and the cartridge 20 can be changed. Note that the mouthpiece 11 may not be changed, but only the cartridge 20 may be changed. In the first embodiment, the inhaler 10 is described to include the mouthpiece 11, but is not limited thereto and the inhaler 10 may not include the mouthpiece 11. Moreover, in the first embodiment, the cartridge 20 and the mouthpiece 11 are configured as different members. However, the cartridge 20 and the mouthpiece 11 may be formed integrally.

Figure 2:
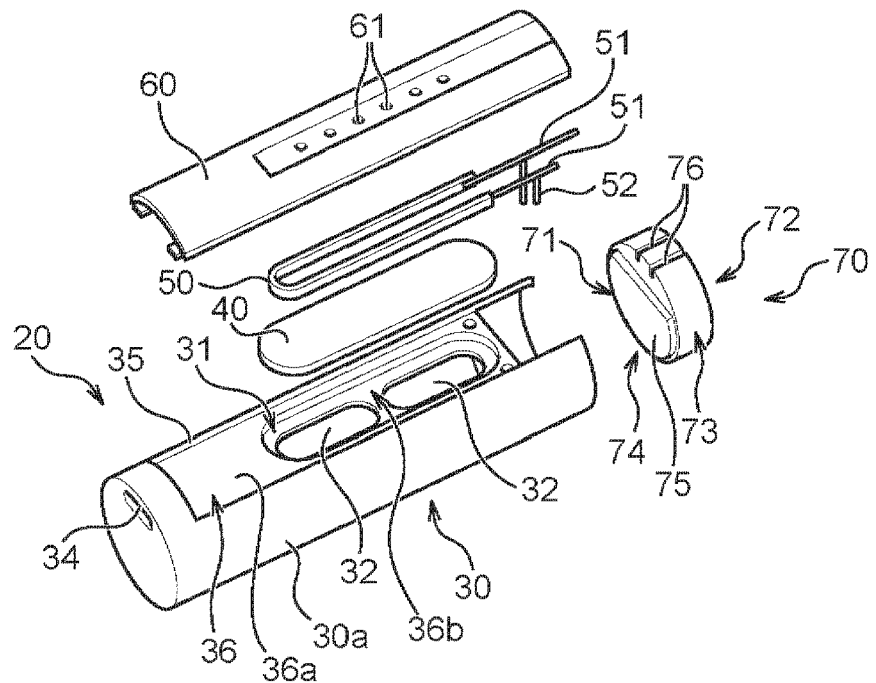
FIG. 2 is an exploded perspective view of a cartridge illustrated in FIG. 1.

FIG. 2 is an exploded perspective view of the cartridge 20 illustrated in FIG. 1. As illustrated in FIG. 2, the cartridge 20 includes a housing 30, a liquid holding member 40, a heater 50, and a cap 70. In addition to the above members, the cartridge 20 may include an outer housing, which is not illustrated, that accommodates the above members therein. In that case, the components illustrated in FIG. 2 constitute part of the cartridge 20.

Figure 3:
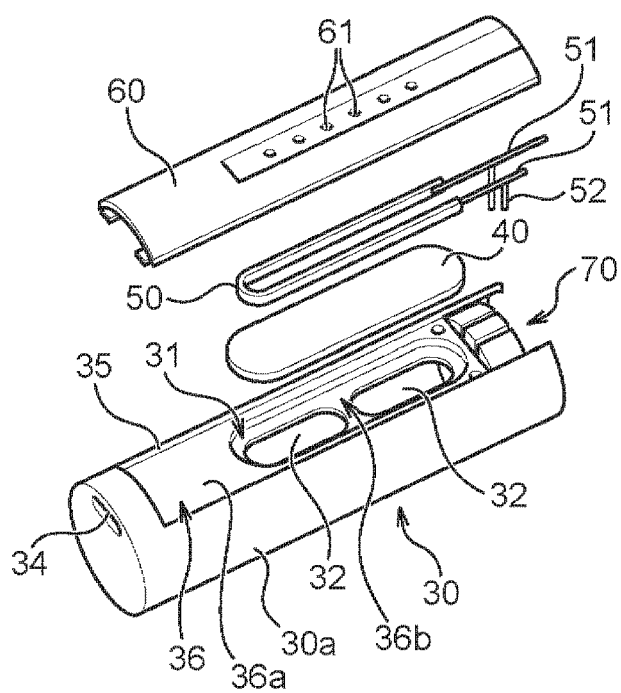
FIG. 3 is a perspective view of a cartridge in a state where a cap is assembled to a housing.
Figure 4:
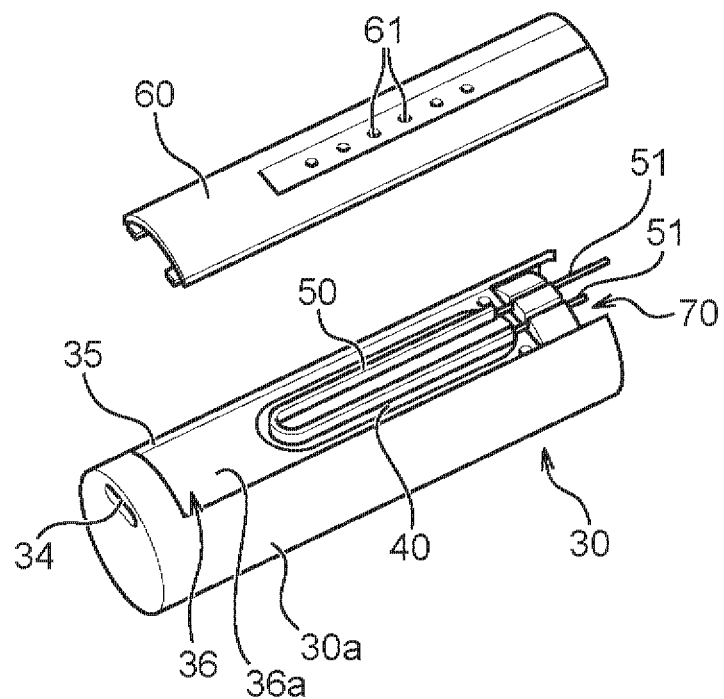
FIG. 4 is a perspective view of a cartridge in a state where a cap, a liquid holding member, and a heater are assembled to a housing.
Figure 5:
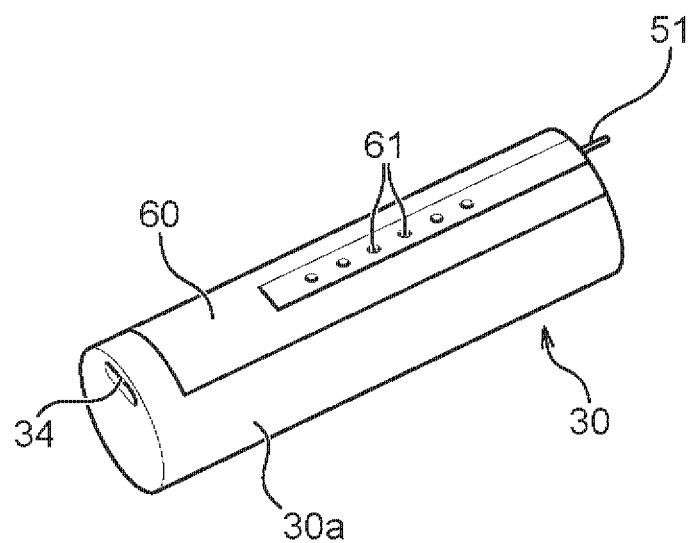
FIG. 5 is a perspective view of a cartridge in a state where all components are assembled.
Figure 6:
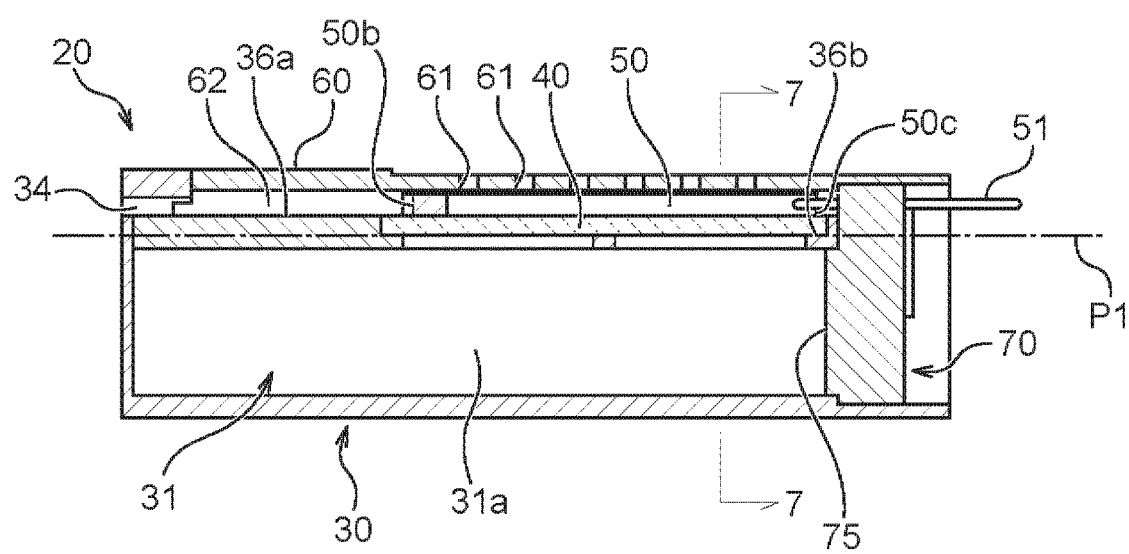
FIG. 6 is a cross-sectional side view of a cartridge in a state where all components are assembled.
Figure 7:
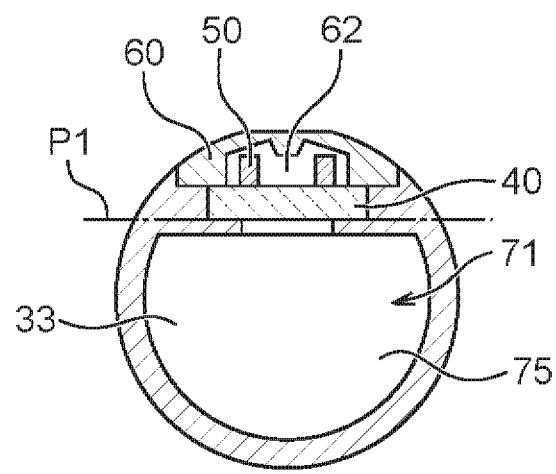
FIG. 7 is a cross-sectional view of the cartridge taken along arrow 7-7 illustrated in FIG. 6.

FIG. 3 is a perspective view of the cartridge 20 in a state where the cap 70 is assembled to the housing 30. FIG. 4 is a perspective view of the cartridge 20 in a state where the cap 70, the liquid holding member 40, and the heater 50 are assembled to the housing 30. FIG. 5 is a perspective view of the cartridge 20 in a state where all the components are assembled. FIG. 6 is a cross-sectional side view of the cartridge 20 in a state where all the components are assembled. FIG. 7 is a cross-sectional view of the cartridge 20 taken along arrow 7-7 illustrated in FIG. 6. Details of the cartridge 20 are described below with reference to FIGS. 2 to 7. Note that, in the present specification, the longitudinal direction indicates a direction in which the cartridge 20 and the battery portion 12 of the inhaler 10 illustrated in FIG. 1 are aligned, and the transverse direction indicates a direction substantially perpendicular to the longitudinal direction. Moreover, in the present specification, the upstream side indicates a side opposite to an air outlet port 34 with reference to the position of the heater 50, or an upstream side in the direction of flow of the aerosol, and the downstream side indicates a side close to the air outlet port 34 with reference to the position of the heater 50, or a downstream side in the direction of flow of the aerosol.

The housing 30 is a member having a substantially cylindrical shape extending in the longitudinal direction of the cartridge 20, and includes a tank 31 that can accommodate a liquid. In the present specification, the internal space of the tank 31 is called an accommodation space 31 a (see FIG. 6). In the first embodiment, the housing 30 and the tank 31 are integrally formed, but are not limited thereto and the housing 30 and the tank 31 may be configured as different components. The housing 30 includes a housing body 30a and a cover member 60 attached to the housing body 30a. The housing body 30a includes a partition member 36 constituting part of the tank 31. The partition member 36 longitudinally partitions an air flow passage 62 defined when the cover member 60 is attached to the housing body 30a (see FIG. 6), and the accommodation space 31 a in the tank 31. The partition member 36 includes a liquid supply port 32 (equivalent to an example of the opening) for supplying the liquid to the accommodation space 31 a in the tank 31. The liquid supply port 32 is opened in the transverse direction of the cartridge 20 to bring the accommodation space 31 a into communication with the air flow passage 62. Note that the communication herein includes communication of liquid and communication of gas.

As illustrated in FIG. 2 or the like, the partition member 36 includes a recess portion to which the liquid holding member 40 is fit, and the liquid supply port 32 is formed through the recess portion. That is, the partition member 36 includes a first surface 36a closest to the cover member 60 for the partition member 36, and a second surface 36b closer to the accommodation space 31 a than the first surface 36a is, and the liquid supply port 32 is formed through the second surface 36b. Note that the first surface 36a and the second surface 36b may have the same height. In that case, the liquid holding member 40 is arranged on the partition member 36 to cover the liquid supply ports 32. The partition member 36 is configured to support the liquid holding member 40 fit to the recess portion of the partition member 36. In the first embodiment, the number of liquid supply ports 32 provided is two, but is not limited thereto and the number of liquid supply ports 32 provided may be any number equal to or more than one. When the number of liquid supply ports 32 provided is plural as in the first embodiment, the partition member 36 partitions the plurality of liquid supply ports 32.

The tank 31 includes an opening 33 opened in the longitudinal direction of the cartridge 20 (see FIG. 7). The opening 33 is formed at an end face of the tank 31 on a side connected to the battery portion 12. In the first embodiment, the opening area of the liquid supply port 32 is configured to be greater than the opening area of the opening 33. In other words, because the liquid supply ports 32 are opened in the transverse direction, it is possible to ensure an opening area greater than the opening 33, which is opened in the longitudinal direction, thereby enabling easy supply of the liquid into the tank 31. Note that, in cases where the number of liquid supply ports 32 is plural, the opening area of the liquid supply ports 32 is the total opening area of the liquid supply ports 32.

Moreover, the housing 30 includes the air outlet port 34 through which the aerosol passes. Specifically, in the first embodiment, the housing body 30a includes the air outlet port 34 through an end surface on a side connected to the mouthpiece 11. The air outlet port 34 communicates with the mouthpiece 11. When the inhaler 10 does not include the mouthpiece 11, the user can directly inhale the aerosol through the air outlet port 34. Note that, in the first embodiment, the air outlet port 34 is formed through the housing body 30a, but is not limited thereto and the air outlet port 34 may be defined by the housing body 30a and the cover member 60 such that the air outlet port 34 is formed when the cover member 60 is attached to the housing body 30a. The air outlet port 34 may be formed through the cover member 60. Moreover, the air outlet port 34 may be formed, for example, through a side surface of the housing 30. Furthermore, the housing body 30a includes a cutout portion 35 formed along the longitudinal direction of the cartridge 20. The cutout portion 35 is covered by the cover member 60. The cutout portion 35 is configured to expose the liquid holding member 40 and the heater 50 when not covered by the cover member 60.

The cover member 60 is a member having a substantially plate shape extending in the longitudinal direction of the cartridge 20. The cover member 60 includes an air inlet port 61 penetrating in the direction of the thickness. The air inlet port 61 is provided at a position facing the partition member 36 of the housing body 30a and the heater 50. In the first embodiment, the air inlet ports 61 are provided at substantially equal intervals along the longitudinal direction of the cover member 60. Note that the number of air inlet ports 61 may be one. The cover member 60, together with the housing body 30a, forms the air flow passage 62 (see FIGS. 6 and 7; equivalent to an example of the space) in which the heater 50 and the liquid holding member 40 are stored. The air inlet ports 61 and the air outlet port 34 are communicated with each other via the air flow passage 62. Note that, in the present embodiment, the air inlet ports 61 are configured to be directly opened to the ambient air and draw the ambient air, but are not limited thereto and may be configured to draw air within an outer housing, which is provided to surround the housing 30. In this case, the housing 30 and the outer housing both may include a means for engaging with the battery portion 12. Alternatively, the housing 30 may include a means for engaging with the battery portion 12 and the outer housing may press the housing 30 against the battery portion 12 such that the housing 30 is engaged with the battery portion 12.

The liquid holding member 40 is a porous member formed, for example, of cotton, glass fiber, or porous ceramic. In the present specification, the "liquid holding member" indicates a porous member that does not have a function of generating heat itself. As illustrated in FIG. 4, the liquid holding member 40 is provided on the cartridge 20 to cover the liquid supply ports 32 of the partition member 36. In other words, the liquid holding member 40 is stacked on the partition member 36 and is supported by the partition member 36. The liquid accommodated in the tank 31 contacts the liquid holding member 40 and is absorbed and held by the liquid holding member 40. In other words, the liquid holding member 40 draws up the liquid, which is accommodated in the tank 31, toward the heater 50. It is preferable that the area of the surface of the liquid holding member 40 facing the liquid supply port 32 be greater than the opening area of the liquid supply port 32. Thus, the entire opening area of the liquid supply port 32 can be covered by the liquid holding member 40 reliably, and supporting the liquid holding member 40 with the partition member 36 is made easy.

The heater 50 generally has a substantially U shape and is arranged on a side opposite to the liquid supply port 32 across the liquid holding member 40. In other words, as illustrated in FIGS. 6 and 7, the heater 50 is arranged between the liquid holding member 40 and the cover member 60. The heater 50 is not limited to the U shape, but may, for example, have a line shape or a planar shape. Specifically, the heater 50 can have an I shape or be in a form in which heaters having an I shape are mutually connected by a lead wire. It is preferable that the heater 50, when having a planar shape, be arranged such that the end surface (plane portion) thereof contacts the liquid holding member 40.

Although not limited, it is preferable that the heater 50 be formed, for example, of a porous metal that can hold liquid. The material of the porous metal used for the heater 50 is not particularly limited insofar as the material can be used as a wick-heater that atomizes the held liquid by electric heating when the user smokes. The heater 50 can be a porous metal object including nickel, nichrome, and stainless steel (SUS). Moreover, as an electrically conductive material that can generate heat upon application of electric power, ceramic, e.g., silicon carbide (SiC), may be used. The heater 50 of the first embodiment has a three-dimensional mesh structure. The three-dimensional mesh structure includes a structure with gaps in which at least some of the gaps are communicated with one another, i.e., an open-cell structure. Such heater 50 of the first embodiment has a function to draw up the liquid by capillary action. Examples of the porous metal object having such an open-cell structure include CELMET (registered trademark) manufactured by Sumitomo Electric Industries, Ltd. CELMET is a porous metal object including nickel (Ni) or a porous metal object including an alloy of nickel and chromium (Cr). Moreover, the heater 50 may be formed such that wires including nickel, nichrome, and stainless steel (SUS) are arranged on the liquid holding member 40 in a mesh pattern or parallel to one another.

The heater 50 is arranged to be at least partially in contact with or in close proximity to the liquid holding member 40, and heats the liquid held by the liquid holding member 40 to generate an aerosol. In cases where the heater 50 is formed of porous metal, when the heater 50 contacts the liquid holding member 40, the heater 50 can absorb and hold the liquid from the liquid holding member 40 and heat the held liquid to generate the aerosol efficiently. Moreover, when the heater 50 is formed of porous metal, the liquid holding member 40 may not be provided on the cartridge 20. In this case, the heater 50 has a liquid holding function in addition to a function as a heating element. Therefore, the heater 50 is arranged in the recess portion of the partition member 36 such that the heater 50 made of a porous metal having a planar shape covers the liquid supply port 32 instead of the liquid holding member 40. Moreover, when the liquid holding member 40 is a porous and rigid body, e.g., porous ceramic, a heater, e.g., of platinum or palladium, may be provided on the liquid holding member 40 in a predetermined pattern, for example, by means of printing or deposition.

Figure 22:
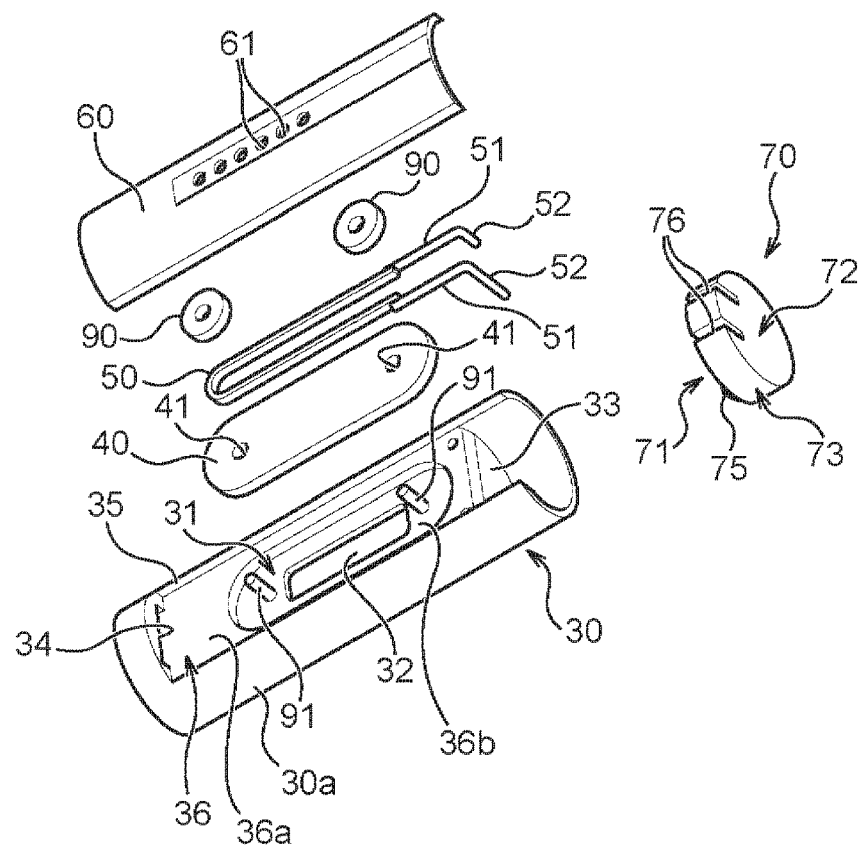
FIG. 22 is an exploded perspective view of a cartridge according to a second embodiment.
Figure 23:
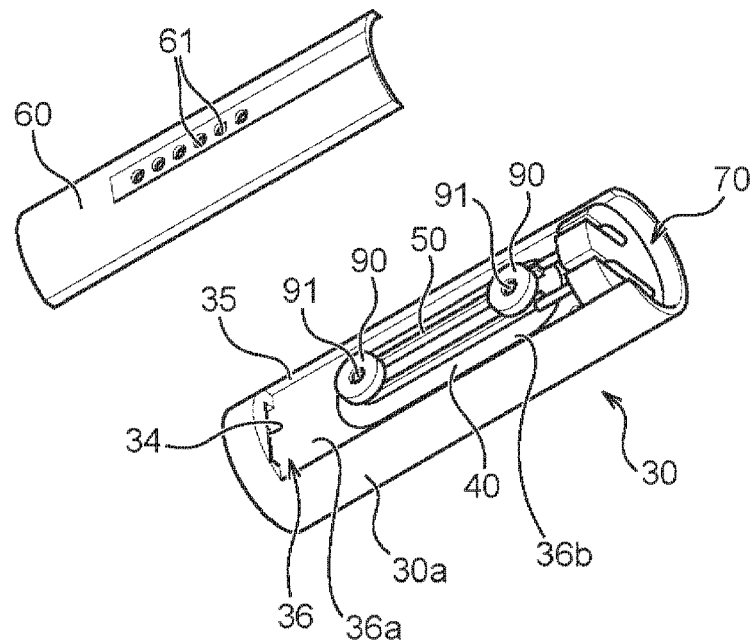
FIG. 23 is a perspective view of a cartridge according to the second embodiment in a state where a cap, a liquid holding member, and a heater are assembled to a housing.

The heater 50 includes a pair of lead wires 51 (equivalent to an example of conductor) for connection to the battery portion 12. The lead wires 51 are received by a pair of reception portions 76, which will be described later, of the cap 70. The heater 50 includes locking portions 52 provided by being branched from the lead wires 51. The locking portions 52 are locked to a second surface 72, which will be described later, of the cap 70 when the lead wires 51 are received in the reception portions 76, and suppress the movement of the heater 50 in the longitudinal direction toward the mouthpiece 11 (air outlet port 34 side). Moreover, the locking portions 52 may be configured to be locked to a first surface 71, which will be described later, of the cap 70. In this case, it is possible to suppress the movement of the heater 50 in the longitudinal direction toward the battery portion 12 side. As illustrated in FIGS. 22 and 23, which will be described later, the locking portions 52 may be formed by bending ends of the lead wires 51.

Next, the cap 70 is described in detail. As illustrated in FIG. 2, the cap 70 is configured to be attachable to and detachable from the cartridge 20. That is, the cap 70 is configured to be a component separate from the components constituting the cartridge 20. Thus, different members can be used for the cap 70 and the housing 30 of the cartridge 20. For example, when the cap 70 is formed of a flexible member, the cap 70 can be easily attached to and detached from the cartridge 20, and when the housing 30 is formed of a non-flexible member (member having high rigidity), the strength of the housing 30 can be increased. In an embodiment, for example, the cap 70 may be configured to be integral with the housing 30 or the tank 31. Moreover, it is preferable that the cap 70 be made of a material having an insulation property, e.g., plastic, or a material having an insulation property and flexibility, e.g., silicon. As illustrated in FIGS. 2 to 7, the cap 70 is configured to be arranged between the tank 31 and the battery portion 12 illustrated in FIG. 1 in the longitudinal direction of the cartridge 20. Moreover, in other words, the cap 70 is provided in a middle of the electric path of a conductor that connects the heater 50 and the battery portion 12. The cap 70 is configured to seal at least part of the space in the tank 31. Specifically, the cap 70 is configured to seal the opening 33 of the tank 31 when attached to the cartridge 20.

As illustrated in FIG. 2, the cap 70 includes the first surface 71, the second surface 72 opposite to the first surface 71, and a cap side surface 73. The cap side surface 73 is a surface connecting the outer circumferential edge of the first surface 71 and the outer circumferential edge of the second surface 72. The cap 70 of the first embodiment generally has a substantially plate shape, but the shape is not limited thereto.

Figure 8:
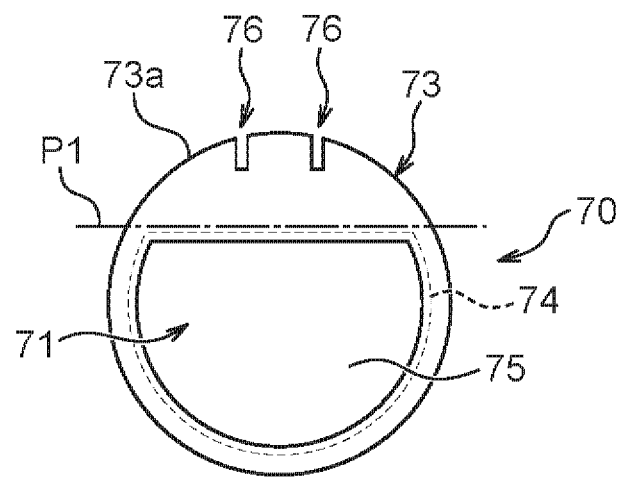
FIG. 8 is a front view of a first surface side of a cap.

The FIG. 8 is a front view of the cap 70 on the first surface 71 side. As illustrated in FIG. 8, the cap 70 includes, on the first surface 71, a seal region 74 that seals at least part of the space in the tank 31. The seal region 74 includes a portion that contacts the edge of the tank 31 constituting the opening 33 and a portion that closes the opening 33. Moreover, the cap 70 includes, on the seal region 74 of the first surface 71, a protrusion portion 75 having a substantially D shape in the front view illustrated in FIG. 8. The protrusion portion 75 is fit to the opening 33 of the tank 31 when the cap 70 is attached to the cartridge 20, and increases the sealing property of the cap 70. That is, as illustrated in FIG. 7, in the first embodiment, the opening 33 includes an opening having a D shape corresponding to the shape of the protrusion portion 75.

As illustrated in FIGS. 2 to 8, the cap 70 includes the pair of reception portions 76 that receives the pair of lead wires 51 of the heater 50. In the first embodiment, the reception portions 76 receive the pair of lead wires 51, but are not limited thereto and the reception portions 76 can receive any conductor that constitutes part of the electric path between the heater 50 and the battery portion 12. In the present specification, the conductor include any conductors for electrically connecting the heater and the battery portion, such as part of the heater 50, the lead wire 51 connected to the heater 50, a lead wire, which is not illustrated, connected to the battery portion 12, a conductive wire (connector) connecting the lead wire 51 of the heater 50 and the lead wire of the battery portion 12, a terminal of the heater 50, a terminal of the battery portion 12, and a combination thereof. As illustrated in FIG. 8, the reception portions 76 are provided on an outer side of the seal region 74. In other words, the reception portions 76 are provided so as not to be positioned in the seal region 74 on the surface of the cap 70. Thus, any conductor (e.g., the lead wire 51) received by the reception portions 76 does not have influence on the seal region 74 that seals the opening 33 of the tank 31. In other words, because the conductor does not pass through the seal region 74, it is not necessary to provide a hole or the like through which the conductor passes in the seal region 74, and the leakage of liquid from the tank 31 can be prevented more reliably.

The reception portions 76 are provided at at least part of the cap side surface 73. In the first embodiment, the reception portions 76 are formed on the cap side surface 73 and have the form of a recess portion penetrating from the first surface 71 to the second surface 72. More specifically, as illustrated in FIG. 8, the reception portions 76 in the form of a recess portion are provided to cut into the central side of the cap 70 relative to an outer circumferential surface 73a of the cap side surface 73. In other words, the reception portions 76 are provided to be dented substantially in a direction of the center when the cap 70 is viewed in the front view of FIG. 8. At least part of the cap side surface 73 is configured to contact each of the pair of conductors connecting the heater 50 and the battery portion 12 when the reception portions 76 receive the pair of lead wires 51. In other words, the cap 70 does not have a hole allowing for the passage of the conductor that connects the heater 50 and the battery portion 12. Therefore, each of the pair of conductors passes through the outer circumferential surface side of the cap 70.

The cap 70 of the first embodiment has a positional relationship to be described below between the seal region 74 and the reception portions 76. That is, as illustrated in FIGS. 6 to 8, when the seal region 74 and the other region of the first surface 71 of the cap 70 are divided by one virtual plane P1 that is parallel to the longitudinal direction of the cartridge 20, the tank 31 is positioned on the seal region 74 side relative to the plane P1 and the reception portions 76 and the heater 50 are positioned on a side opposite to the seal region 74 relative to the plane P1. That is, the cap 70 of the first embodiment has a positional relationship in which the seal region 74 is clearly distinguished from the reception portions 76 by the one plane P1. Therefore, the reception portions 76 do not have influence on the seal region 74, and the leakage of liquid from the tank 31 attributable to the reception portions 76 can be prevented more reliably.

Next, a procedure for assembling the cartridge 20 is described. First, as illustrated in FIG. 3, the opening 33 of the tank 31 is closed by cap 70. Thus, the seal region 74 of the cap 70 seals the opening 33, and the leakage of liquid through the opening 33 is prevented. Next, a liquid, which is an aerosol source, is supplied into the accommodation space 31a through the liquid supply ports 32. Then, as illustrated in FIG. 4, the liquid holding member 40 is arranged to cover the liquid supply ports 32. The partition member 36 has a recess portion formed of a step between the first surface 36a and the second surface 36b. Therefore, even if the liquid is somewhat spilled through the liquid supply ports 32 of the tank 31, the liquid is retained in the recess portion. When the liquid holding member 40 is arranged to cover the liquid supply ports 32, the liquid holding member 40 holds the liquid, preventing leakage of the liquid from the tank 31. In other words, the cartridge 20 can hold the liquid in an amount of equal to or more than the volume of the tank 31 by means of the liquid holding member 40.

Meanwhile, if the liquid holding member 40 is arranged to cover the liquid supply ports 32 and then the liquid is supplied to the accommodation space 31a through the opening 33, there is a possibility that the liquid could be leaked from a gap between the liquid holding member 40 and the liquid supply ports 32 or through the liquid holding member 40. Moreover, in this case, because the liquid is supplied to the accommodation space 31a and then the cap 70 is attached to the opening 33, the pressure in the accommodation space rises when the opening 33 is closed by the cap 70, thereby possibly accelerating leakage of the liquid through the liquid supply ports 32. Accordingly, when the opening 33 of the tank 31 is closed by the cap 70 and the liquid is supplied into the accommodation space 31a as in the manner of the present embodiment, the leakage of the liquid from the tank 31 can be prevented.

Note that when the heater 50 is formed of porous metal as described above, the cartridge 20 may not include the liquid holding member 40. In this case, the heater 50 made of a porous metal having a planar shape is arranged in the recess portion of the partition member 36 such that the heater 50 covers the liquid supply ports 32 instead of the liquid holding member 40. Moreover, in this case, because the heater 50 directly contacts the housing 30 (in the first embodiment, partition member 36), the contact portion of the housing 30 may be formed of a heat-resistant material or may be covered with a heat-resistant material.

Next, the heater 50 is arranged on the liquid holding member 40. At this time, the lead wires 51 of the heater 50 are received by the reception portions 76. In other words, the lead wires 51 of the heater 50 are engaged with the reception portions 76 of the cap 70 to bring the heater 50 into contact with the surface of the liquid holding member 40. Because the reception portions 76 have the shape of a recess portion formed on the cap side surface 73, the lead wires 51 can be easily arranged in the reception portions 76 from the side of the cap 70.

Finally, as illustrated in FIGS. 5 to 7, the cover member 60 is attached to the housing body 30a to cover the cutout portion 35. Thus, assembling of the cartridge 20 is completed. In a state where all of the components of the cartridge 20 are assembled, as illustrated in FIGS. 6 and 7, the air flow passage 62 is defined by the cover member 60 and the housing body 30a. When electric power is supplied to the heater 50, the liquid held by the liquid holding member 40 is heated, and an aerosol is generated. Moreover, when the heater 50 can be used as a wick-heater, the liquid held by the heater 50 is heated and an aerosol is generated. When the user inhales the air through the mouthpiece 11, the air flowing in through the air inlet ports 61 of the cover member 60 passes through the air flow passage 62 and flows out through the air outlet port 34 together with the aerosol present in the air flow passage 62. Thus, the aerosol is supplied into the user's mouth.

As described above, the cap 70 of the cartridge 20 includes the seal region 74 and the reception portions 76 provided on an outer side of the seal region 74. Therefore, it is not necessary to provide, in the seal region 74, a hole or the like for holding the conductor (e.g., the lead wires 51) to be received by the reception portions 76. Accordingly, the leakage of the liquid in the tank 31 toward the battery portion 12 side through the reception portions 76 can be prevented more reliably.

Moreover, in the cartridge 20 of the present embodiment, the liquid supply ports 32 are opened in the transverse direction, and the reception portions 76 are provided at at least part of the cap side surface 73 of the cap 70. Therefore, when the liquid holding member 40 and the heater 50 are assembled to the cartridge 20, the liquid supply ports 32 can be covered with the liquid holding member 40 in the transverse direction, and the lead wires 51 can be arranged in the reception portions 76 from the side of the cap 70. Therefore, as compared with the case where the lead wires 51 are inserted into the reception portions having a through-hole shape formed in the longitudinal direction, the liquid holding member 40 and the heater 50 can be easily assembled to the cartridge 20.

Moreover, in the case of the cartridge 20 of the present embodiment, the pair of lead wires 51 are arranged to be spaced apart so as not to be mutually electrically connected. Specifically, in the present embodiment, each of the pair of reception portions 76 receives the lead wire 51. However, it is not limited thereto, but the number of reception portions 76 may be one. In that case, the pair of lead wires 51 are received by the one reception portion 76 without mutual electrical contact. Moreover, the pair of lead wires 51 may be covered with an insulation material so as not to electrically contact each other. The shape of the reception portions 76 may be any shape that can receive the conductor.

Note that the cap 70 of the first embodiment has a substantially plate shape including the first surface 71, the second surface 72, and the cap side surface 73, but the shape is not limited thereto insofar as the reception portions 76 are provided on an outer side of the seal region 74. For example, the cap 70 may be any shape, e.g., a spherical shape or a columnar shape having a spherical surface at an end. Moreover, the cartridge 20 of the first embodiment is configured such that the lead wires 51 of the heater 50 are arranged on the reception portions 76 of the cap 70, but is not limited thereto and a conductor (e.g., a connector member) or the like different from the heater 50 and the lead wires 51 may be arranged on the reception portions 76, and the conductor may be connected to the lead wires 51 of the heater 50. That is, in this case, a conductor (e.g., a connector member) is arranged between the first surface 71 and the second surface 72 of the cap 70.

Next, a positional relationship between the accommodation space 31a, the air flow passage 62, the partition member 36, the heater 50, the air inlet ports 61, and the air outlet port 34 in the transverse direction of the cartridge 20 illustrated in FIGS. 2 to 8 is described. As illustrated in FIGS. 2 to 6, the cartridge 20 includes the air inlet ports 61 (cover member 60), the air flow passage 62, the partition member 36, and the accommodation space 31a of the tank 31 in this order along the transverse direction. The heater 50 is arranged between the air inlet ports 61 and the partition member 36 and within the air flow passage 62.

Figure 9:
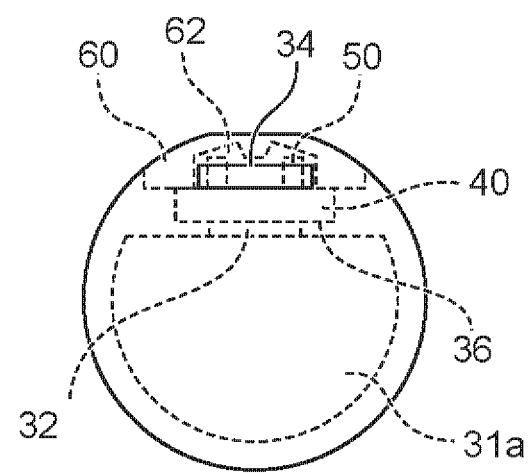
FIG. 9 is a view of the cartridge according to the first embodiment when viewed from an end surface where an air outlet port is provided.

FIG. 9 is a view of the cartridge 20 according to the first embodiment when viewed from an end surface where the air outlet port 34 is provided. As described with regard to FIG. 6, when the user inhales the air through the mouthpiece 11 or the air outlet port 34, the air flowing in through the air inlet ports 61 of the cover member 60 passes through the air flow passage 62 and flows toward the air outlet port 34. At this time, in order for the air flowing in through the air inlet ports 61 to efficiently deliver the aerosol, which is generated by the heater 50, to the air outlet port 34, it is preferable that the air flowing in through the air inlet ports 61 flow in the air flow passage 62 to pass through the vicinity or inside the heater 50. In other words, when the air flowing in through the air inlet ports 61 flows toward the air outlet port 34 without passing through the vicinity or inside the heater 50, the air cannot sufficiently entrain the airborne aerosol in the vicinity of the heater 50. Therefore, in the first embodiment, as illustrated in FIG. 9, the position of the air outlet port 34 in the transverse direction is provided to be partially overlapped in the longitudinal direction with the position of the heater 50 in the transverse direction.

Moreover, as illustrated in FIG. 6, it is preferable that at least part of the heater 50 be present at the same position as any one of the air inlet ports 61 or positioned on the air outlet port 34 side with respect to any one of the air inlet ports 61 in the longitudinal direction. In other words, as illustrated in FIG. 6, when an end of the heater 50 close to the air outlet port 34 in the longitudinal direction is defined as a first end 50*b* and an end far from the air outlet port 34 is defined as a second end 50*c*, at least one of the air inlet ports 61 is preferably provided on an upstream side of the first end 50*b* of the heater 50 with respect to the longitudinal position. Moreover, the air inlet ports 61 may be provided on an upstream side of the second end 50*c* of the heater 50 with respect to the longitudinal position. Note that the air outlet port 34 herein is not the opening of the air outlet port 34 exposed to the outside of the cartridge 20, but is an interface between the air flow passage 62 and the air outlet port 34, i.e., an opening of the air outlet port 34 to the air flow passage 62.

For example, when the position of the air outlet port 34 in the transverse direction is present on the air inlet port 61 side relative to the position of the heater 50 in the transverse direction, the air flowing in through the air inlet ports 61 passes through the shortest passage to the air outlet port 34 and hardly contacts the heater 50. Meanwhile, when the air outlet port 34 and the heater 50 have the positional relationship illustrated in FIG. 9, at least part of the heater 50 is arranged in the air flow passage 62 through which the air flowing in through the air inlet ports 61 flows out through the air outlet port 34, and therefore the air from the air inlet ports 61 easily contacts the heater 50.

Figure 10:
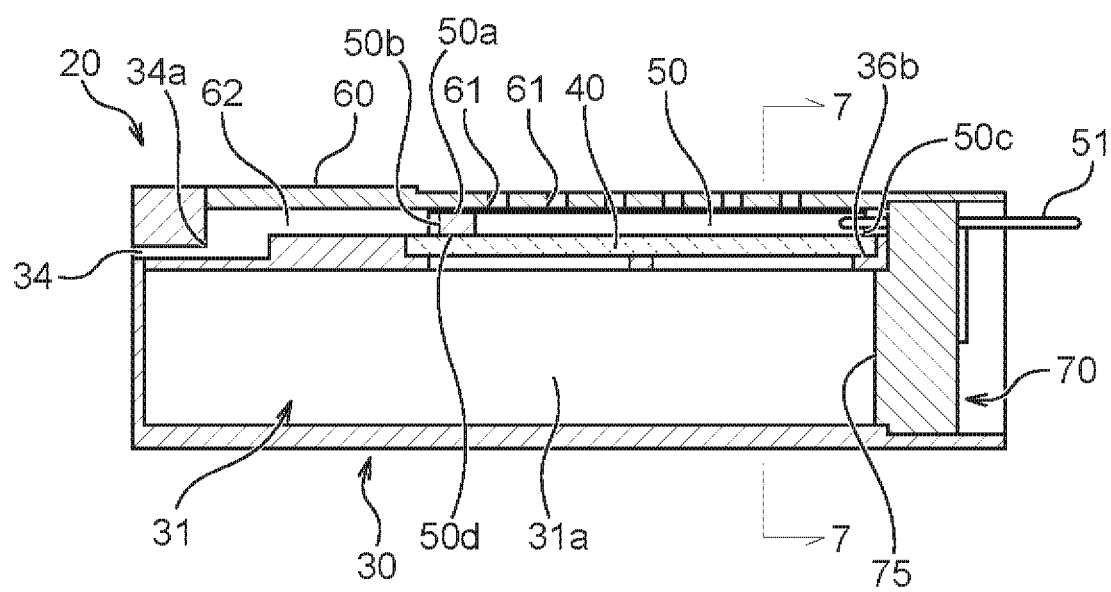
FIG. 10 is a cross-sectional side view of a cartridge illustrating an example of a different positional relationship between an air outlet port and a heater.

The positional relationship of the air outlet port 34 and the heater 50 in the transverse direction is not limited to the above. FIG. 10 is a cross-sectional side view of the cartridge 20 illustrating an example of a different positional relationship between the air outlet port 34 and the heater 50. As illustrated in FIG. 10, in the case of this cartridge 20, the air outlet port 34 is positioned on the accommodation space 31 *a* side relative to the heater 50 in the transverse direction. Specifically, an upper end 34*a* of the air outlet port 34 close to the air inlet port 61 side is positioned on the accommodation space 31 *a* side in the transverse direction relative to an upper end 50*a* of the heater 50 close to the air inlet port 61 side. In the example illustrated in FIG. 10, the upper end 34*a* of the air outlet port 34 close to the air inlet port 61 side is positioned on the accommodation space 31 *a* side in the transverse direction relative to a lower end 50*d* of the heater 50 far from the air inlet port 61 side.

When the air outlet port 34 and the heater 50 have the positional relationship illustrated in FIG. 10, the upper end 34*a* of the air outlet port 34 is positioned on the accommodation space 31 *a* side in the transverse direction relative to the lower end 50*d* of the heater 50. Therefore, the air from the air inlet ports 61 easily contacts the heater 50. Eventually, the aerosol generated through heating by the heater 50 can be efficiently delivered to the air outlet port 34.

Figure 11:
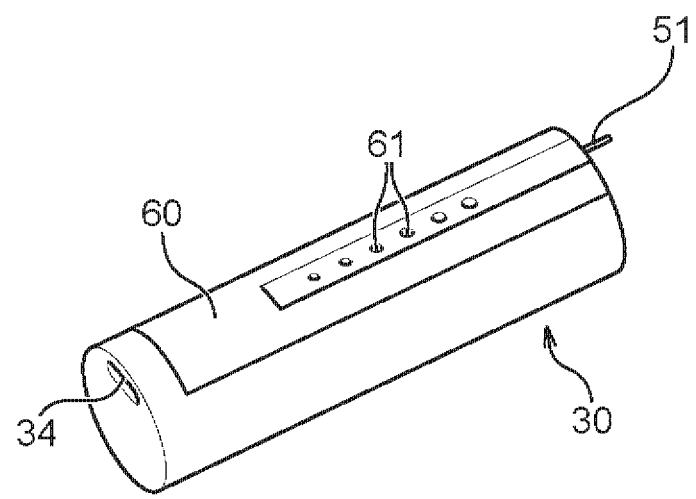
FIG. 11 is a plan view illustrating a different form of a cover member.
Figure 12:
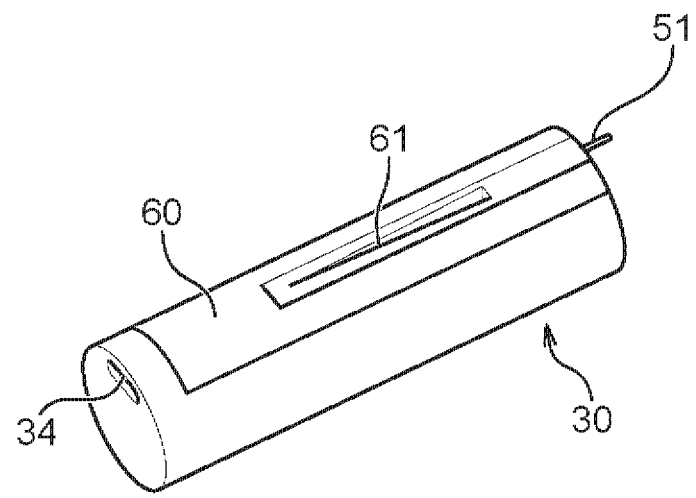
FIG. 12 is a plan view illustrating a different form of a cover member.

Next, another form example of the cover member 60 illustrated in FIGS. 2 to 10 is described. FIGS. 11 and 12 are plan views illustrating a different form of the cover member 60. As illustrated in FIG. 11, the cover member 60 includes a plurality of air inlet ports 61 provided along the longitudinal direction. Moreover, the cover member 60 illustrated in FIG. 12 includes a single air inlet port 61 provided along the longitudinal direction.

In cases where the air inlet ports 61 have the same opening area, when the user inhales the air through the mouthpiece 11 (see FIG. 1) or the air outlet port 34, the amount of air flowing in through an air inlet port 61 positioned close to the air outlet port 34 becomes larger than the amount of air flowing in through an air inlet port 61 positioned far from the air outlet port 34. Similarly, in cases where a single air inlet port 61 has a constant area per unit length in the longitudinal direction, when the user inhales the air through the mouthpiece 11 (see FIG. 1) or the air outlet port 34, the amount of air flowing in through a portion of the air inlet port 61 positioned close to the air outlet port 34 is larger than the amount of air flowing in through a portion of the air inlet port 61 positioned far from the air outlet port 34.

In contrast, the air inlet ports 61 illustrated in FIGS. 11 and 12 have an opening area formed to be smaller toward the air outlet port 34. In other words, the area of an air inlet port 61 on a side proximal to the air outlet port 34 is smaller than the area of an air inlet port 61 on a side distal to the air outlet port 34. Thus, the amount of air flowing in through each of the air inlet ports 61 or the amount of air flowing in from each position of the single air inlet port 61 in the longitudinal direction can be equalized. As a result, the air can contact the entire heater 50, and thus the aerosol can be delivered efficiently.

Figure 13:
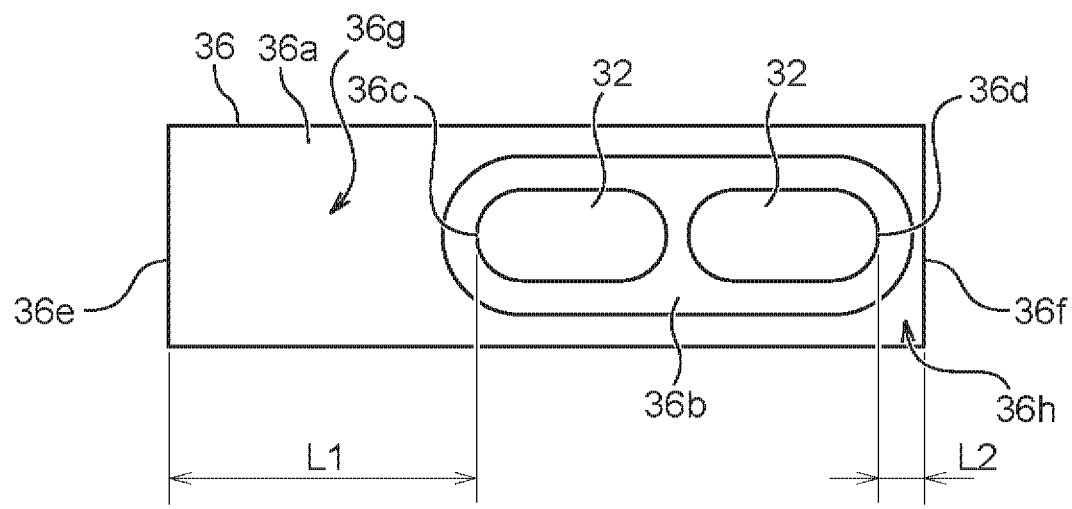
FIG. 13 is a plan view of a partition member.

Next, the shape of the partition member 36 of the cartridge 20 illustrated in FIGS. 2 to 8 is described in detail. FIG. 13 is a plan view of the partition member 36. As illustrated in FIG. 13, the partition member 36 includes a downstream-side end 36*e* positioned on a side closest to the air outlet port 34 and an upstream-side end 36*f* positioned on a side farthest from the air outlet port 34. The downstream-side end 36*e* is an end that contacts the housing 30 in the longitudinal direction as illustrated in FIG. 6. The upstream-side end 36*f* is an end that contacts the cap 70. Moreover, the liquid supply port 32 of the partition member 36 includes a downstream-side opening edge 36*c* positioned on a side closest to the air outlet port 34 and an upstream-side opening edge 36*d* positioned on a side farthest from the air outlet port 34. Note that, when a plurality of liquid supply ports 32 is present as illustrated in FIG. 13, the downstream-side opening edge 36*c* is an opening edge positioned on the most downstream side of the plurality of liquid supply ports 32 and the upstream-side opening edge 36*d* is an opening edge positioned on the most upstream side of the plurality of liquid supply ports 32. Furthermore, the partition member 36 includes an upstream portion 36*h* positioned between the upstream-side opening edge 36*d* of the liquid supply port 32 and the upstream-side end 36*f*, and a downstream portion 36*g* positioned between the downstream-side opening edge 36*c* of the liquid supply port 32 and the downstream-side end 36*e*.

In the present embodiment, as illustrated in FIG. 13, the partition member 36 is formed such that the liquid supply ports 32 are generally shifted to the upstream side. More specifically, the liquid supply ports 32 are formed on the partition member 36 such that distance L2 between the upstream-side opening edge 36*d* of the liquid supply ports 32 and the upstream-side end 36*f* of the partition member 36 is smaller than distance L1 between the downstream-side opening edge 36*c* of the liquid supply ports 32 and the downstream-side end 36*e* of the partition member 36. The distance L2 between the upstream-side opening edge 36*d* of the liquid supply ports 32 and the upstream-side end 36f of the partition member 36 can be said to be a longitudinal length of the upstream portion 36h of the partition member 36. Similarly, the distance L1 between the downstream-side opening edge 36c of the liquid supply ports 32 and the downstream-side end 36e of the partition member 36 can be said to be a longitudinal length of the downstream portion 36g of the partition member 36. Accordingly, the longitudinal length of the upstream portion 36h is shorter than the longitudinal length of the downstream portion 36g.

Figure 14:
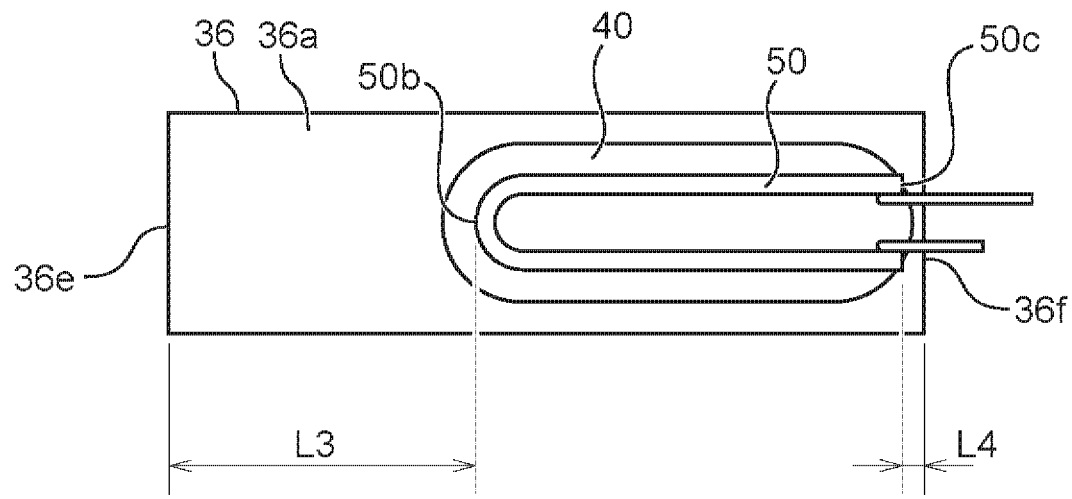
FIG. 14 is a plan view of a partition member, a liquid holding member, and a heater.

FIG. 14 is a plan view of the partition member 36, the liquid holding member 40, and the heater 50. As illustrated in FIG. 14, the liquid holding member 40 is provided in the recess portion of the partition member 36, and the heater 50 is arranged on the liquid holding member 40. The heater 50 includes the first end 50b (equivalent to an example of the downstream-side heater end) positioned on a side closest to the air outlet port 34 and the second end 50e (equivalent to an example of the upstream-side heater end) positioned on a side farthest from the air outlet port 34.

In the present embodiment, as illustrated in FIG. 14, the heater 50 is also arranged to be generally shifted to the upstream side. More specifically, distance L4 between the second end 50c and the upstream-side end 36f of the partition member 36 is smaller than distance L3 between the first end 50b and the downstream-side end 36e of the partition member 36.

The inhaler 10 illustrated in FIG. 1 is held by the user such that, when the user inhales the air through the mouthpiece 11, the cartridge 20 is normally at a position lower than the mouthpiece 11, i.e., the upstream side is positioned below. Accordingly, if the liquid supply ports 32 are provided to be shifted to the downstream side, the position of the liquid supply ports 32 at a time when the inhaler 10 is used is positioned above as compared with the case where the liquid supply ports 32 are provided to be shifted to the upstream side. In this case, when the inhaler 10 is used, the liquid in the tank 31 is retained on the upstream side (lower side) by gravity. Therefore, when the liquid in the tank 31 is reduced, there is a possibility that the liquid hardly contacts the liquid holding member 40.

Meanwhile, if the liquid supply ports 32, the liquid holding member 40, and the heater 50 are provided across the entire partition member 36 in the longitudinal direction, the heater 50 is arranged in close proximity to the air outlet port 34. In this case, there is a possibility that the aerosol generated near the first end 50b of the heater 50 is not sufficiently cooled, but is guided at high temperature to the air outlet port 34 and reaches the user's mouth. Moreover, in cases where the liquid supply ports 32, the liquid holding member 40, and the heater 50 are provided across the entire partition member 36 in the longitudinal direction, when the liquid in the tank 31 is reduced, the liquid is hardly absorbed by a downstream-side (upper side) portion of the liquid holding member 40. That is, because the liquid becomes easily held by an upstream-side (lower side) portion of the liquid holding member 40, the heat near the first end 50b of the heater 50 hardly make a contribution to generating the aerosol, possibly resulting in a reduction in efficiency.

Therefore, in the first embodiment, as illustrated in FIG. 10, the liquid supply ports 32 are arranged to be generally shifted to the upstream side such that the liquid supply ports 32 are positioned below when the inhaler 10 is used. When the inhaler 10 is used, the liquid in the tank 31 is retained on the upstream side (lower side) by gravity. Therefore, even when the liquid in the tank 31 is reduced, the liquid can be efficiently held by the liquid holding member 40 via the liquid supply ports 32. Eventually, the liquid can be efficiently heated by the entire heater 50 to generate the aerosol.

Moreover, in the first embodiment, the liquid supply ports 32 and the heater 50 are not provided on the downstream side of the partition member 36. Therefore, it is possible to increase the distance over which the aerosol generated by the heater 50 reaches the air outlet port 34 (see FIGS. 2 to 8). As a result, the distance over which the generated aerosol reaches the user's mouth is increased, and the time for cooling the aerosol can be increased.

As illustrated in FIGS. 13 and 14, it is preferable that the area of the surface of the liquid holding member 40 facing the liquid supply ports 32 be smaller than the area of the surface of the partition member 36 where the liquid supply ports 32 are provided (in the first embodiment, the surface including the first surface 36a and the second surface 36b). Thus, a sufficient amount of liquid to be held per unit area of the liquid holding member 40 can be ensured. In addition, because the heater 50 and the liquid supply ports 32 are positioned to face each other across the liquid holding member 40, the liquid is directly supplied to a portion of the liquid holding member 40 that is easily heated by the heater 50, and it is possible to suppress depletion of the liquid (aerosol source) held by the liquid holding member 40 during heating by the heater 50.

Figure 15:
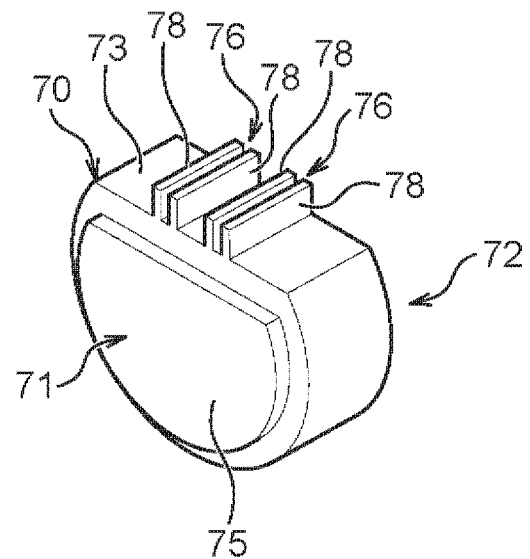
FIG. 15 is a perspective view illustrating a different form of the cap.

Next, another form example of the cap 70 illustrated in FIGS. 2 to 8 is described. FIG. 15 is a perspective view illustrating a different form of the cap 70. As illustrated in FIG. 15, the cap 70 differs from the cap 70 illustrated in FIGS. 2 to 8 in shape of the reception portions 76. That is, in the case of the cap 70 illustrated in FIG. 15, the shape of the first surface 71 and the second surface 72 is formed in a substantially semicircular shape, and the cap side surface 73 includes two reception portions 76. Specifically, each of the reception portions 76 of the cap 70 includes a pair of projections 78 projecting from the cap side surface 73. A recess portion is formed between the pair of projections 78, and the lead wires 51 of the heater 50 illustrated in FIG. 2 or the like are received in the recess portions. Thus, the pair of lead wires 51 is arranged to be spaced apart without mutual electrical contact. Note that three projections 78 may be provided on the cap side surface 73. In this case, two reception portions 76 are formed between the three projections 78. Moreover, the number of reception portions 76 may be one. In that case, the pair of lead wires 51 is received by one reception portion 76 so as not to electrically contact each other.

Also in the case of the cap 70 illustrated in FIG. 15, similar to the cap 70 illustrated in FIGS. 2 to 8, the reception portions 76 are provided on an outer side of the seal region 74. Therefore, the leakage of the liquid in the tank 31 to the battery portion 12 side via the reception portions 76 can be prevented more reliably. Moreover, because the reception portions 76 are provided at at least part of the cap side surface 73 of the cap 70, the lead wires 51 can be arranged in the reception portions 76 from the side of the cap 70, and the heater 50 can be easily assembled to the cartridge 20. Furthermore, because the cap 70 illustrated in FIG. 15 is a plate-shaped body having a substantially semicircular shape, it is possible to increase the area of the air flow passage through which the internal space 62, which is formed by the cover member 60 and the housing 30, communicates with the space on the battery portion 12 side when the cap 70 is assembled to the cartridge 20. Accordingly, for example, when the air inlet port is provided on the upstream side (battery portion 12 side) relative to the cap 70, the air can be supplied to the internal space 62 from the upstream side of the cap 70. Note that, in this case, the cover member 60 may not include the air inlet port 61.

Moreover, in the case of the cap 70 illustrated in FIG. 15, a conductor (e.g., a connector member) or the like different from the heater 50 and the lead wire 51 may be arranged on the reception portion 76, and the conductor may be connected to the lead wire 51 of the heater 50. That is, in this case, the conductor (e.g., a connector member) is arranged between the first surface 71 and the second surface 72 of the cap 70.

Figure 16:
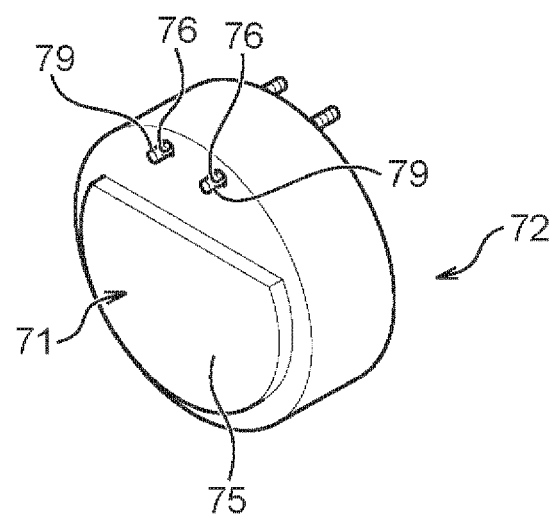
FIG. 16 is a perspective view illustrating a different form of the cap.

FIG. 16 is a perspective view illustrating a different form of the cap 70. As illustrated in FIG. 16, this cap 70 differs from the cap 70 illustrated in FIGS. 2 to 15 in shape of the reception portions 76. That is, the reception portions 76 of the cap 70 illustrated in FIG. 16 have a hole shape penetrating between the first surface 71 and the second surface 72. Moreover, the reception portions 76 of the cap 70 receive connector members 79 (equivalent to an example of the conductor) extending between the first surface 71 and the second surface 72. The connector member 79 is configured to have one end connected to the lead wire 51 of the heater 50 and the other end connected to a lead wire or a terminal, which is not illustrated, of the battery portion 12 so as to conduct the lead wire 51 to the battery portion 12.

When the cap 70 illustrated in FIG. 16 is used in the cartridge 20, the lead wires 51 of the heater 50 are formed to be somewhat shorter than the lead wires 51 illustrated in FIGS. 2 to 7. When the heater 50 is arranged on the liquid holding member 40, the lead wires 51 are brought into contact with or connected to ends of the connector members 79 provided in the cap 70. Thus, the lead wires 51 are conducted to the battery portion 12.

Similar to the cap 70 illustrated in FIGS. 2 to 15, the cap 70 illustrated in FIG. 16 also includes the reception portions 76 on an outer side of the seal region 74. Therefore, the leakage of the liquid in the tank 31 to the battery portion 12 side through the reception portions 76 can be prevented more reliably. Moreover, because the cap 70 illustrated in FIG. 16 includes the connector members 79 arranged in the reception portions 76, the heater 50 can be easily assembled to the cartridge 20 so as to be conducted to the battery portion 12. As illustrated in FIG. 16, when the connector members 79 have a length protruding from the first surface 71 and the second surface 72 of the cap 70, a recess portion or the like by which the lead wires 51 can be connected in the transverse direction of the cartridge 20 may be provided at ends of the connector members 79. In that case, when the liquid holding member 40 and the heater 50 are assembled to the cartridge 20, the liquid supply ports 32 may be covered with the liquid holding member 40 in the transverse direction, and the lead wires 51 may be connected to the connector members 79 in the transverse direction. Therefore, the liquid holding member 40 and the heater 50 can be further easily assembled to the cartridge 20. Note that the connector members 79 illustrated in FIG. 16 have a length protruding from the first surface 71 and the second surface 72 of the cap 70, but, for example, may have a length fit within the reception portions 76 so as to be accommodated in the reception portions 76. In this case, when the ends of the lead wires 51 of the heater 50 are inserted into the reception portions 76, the ends of the lead wires 51 are guided by the reception portions 76 toward the connector members 79, and the ends of the lead wires 51 are brought into contact with or connected to the connector members 79.

Figure 17:
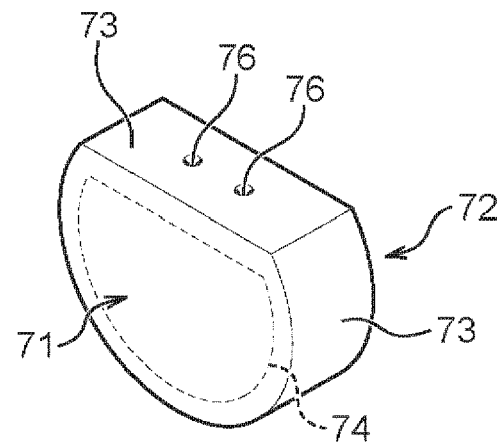
FIG. 17 is a perspective view illustrating a different form of the cap.
Figure 18:
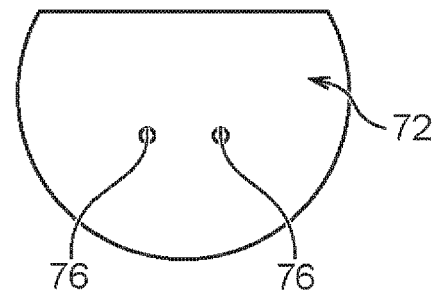
FIG. 18 is a front view of the cap of FIG. 17 when viewed from a second surface side.
Figure 19:
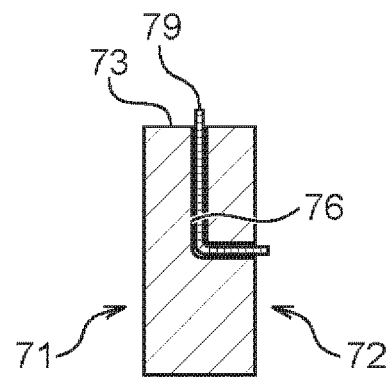
FIG. 19 is a cross-sectional side view of the cap of FIG. 17.

FIG. 17 is a perspective view illustrating a different form of the cap 70. FIG. 18 is a front view of the cap of FIG. 17 when viewed from the second surface 72 side. FIG. 19 is a cross-sectional side view of the cap of FIG. 17. As illustrated in FIG. 17, in the case of this cap 70, the first surface 71 includes the seal region 74, and the first surface 71 and the second surface 72 are formed to have a substantially semicircular shape. The reception portions 76, when viewed in side cross-section illustrated in FIG. 19, have a form of a hole having a substantially L shape penetrating through the cap side surface 73 and the second surface 72.

As illustrated in FIG. 19, the reception portion 76 of the cap 70 receives the connector member 79 (equivalent to an example of the conductor) extending between the cap side surface 73 and the second surface 72. The connector member 79 is configured to have one end connected to the lead wire 51 of the heater 50 and the other end connected to a lead wire or terminal, which is not illustrated, of the battery portion 12 so as to conduct the lead wire 51 to the battery portion 12. In the illustrated example, the connector member 79 is configured to protrude from the hole of the reception portion 76, but is not limited thereto and may be configured such that the end of the connector member 79 is positioned in the reception portion 76. Note that, regarding the cap 70 illustrated in FIGS. 17 and 18, illustration of the connector members 79 is omitted.

In cases where the cap 70 illustrated in FIG. 17 is used in the cartridge 20, when the heater 50 is arranged on the liquid holding member 40, the lead wires 51 are brought into contact with or connected to the ends of the connector members 79 provided in the cap 70. Because the lead wire or terminal, which is not illustrated, of the battery portion 12 is conducted to the ends of the connector members 79 positioned on the second surface 72 side, the lead wires 51 are conducted to the battery portion 12. Note that, when the ends of the connector members 79 are configured to be positioned in the reception portions 76, the lead wires 51 are formed in an L shape such that the ends of the lead wires 51 enter the holes of the reception portions 76 formed in the cap side surface 73 when the heater 50 is arranged on the liquid holding member 40. Thus, the lead wires 51 are brought into contact with or connected to the ends of the connector members 79 such that the heater 50 is conducted to the battery portion 12.

Similar to the cap 70 illustrated in FIGS. 2 to 16, the cap 70 illustrated in FIG. 17 also includes the reception portions 76 on an outer side of the seal region 74. Therefore, the leakage of the liquid in the tank 31 to the battery portion 12 side via the reception portions 76 can be prevented more reliably. Moreover, because the cap 70 illustrated in FIG. 17 includes the connector members 79 arranged in the reception portions 76, the heater 50 can be easily assembled to the cartridge 20 so as to be conducted to the battery portion 12. Furthermore, because the cap illustrated in FIG. 17 is a plate-shaped body having a substantially semicircular shape, it is possible to increase the area of the air flow passage through which the internal space 62, which is formed by the cover member 60 and the housing 30, communicates with the space on the battery portion 12 side when the cap 70 is assembled to the cartridge 20. Accordingly, for example, when the air inlet port is provided on the upstream side (battery portion 12 side) of the cap 70, the air can be supplied to the internal space 62 from the upstream side of the cap 70. Note that, in this case, the cover member 60 may not include the air inlet port 61. Moreover, the cap 70 illustrated in FIG. 17 does not include the protrusion portion 75 of the cap 70 illustrated in FIGS. 2 to 16, but may include the protrusion portion 75 in the seal region 74. The reception portions 76 have a form of a hole penetrating through the cap side surface 73 and the second surface 72, but may instead have a form of a recess portion penetrating through the cap side surface 73 and the second surface 72.

Figure 20:
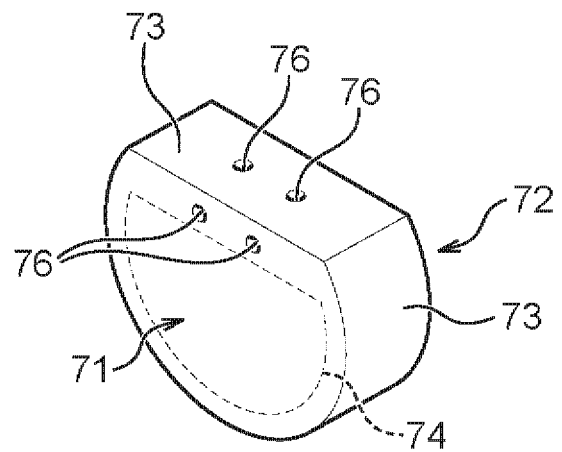
FIG. 20 is a perspective view illustrating a different form of the cap.
Figure 21:
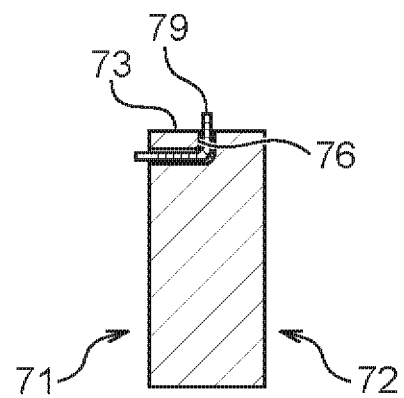
FIG. 21 is a cross-sectional side view of the cap of FIG. 20.

FIG. 20 is a perspective view of a different form of the cap 70. FIG. 21 is a cross-sectional side view of the cap of FIG. 20. As illustrated in FIG. 20, this cap 70 is similar to the cap 70 illustrated in FIGS. 17 to 19 such that the first surface 71 includes the seal region 74, and the first surface 71 and the second surface 72 are formed to have a substantially semicircular shape. Meanwhile, this cap 70 differs from the cap 70 illustrated in FIGS. 17 to 19 in that the reception portions 76 have a form of a hole having a substantially L shape penetrating through the cap side surface 73 and the first surface 71 when viewed in side cross-section illustrated in FIG. 21. As illustrated in FIG. 20, the holes constituting the reception portions 76 formed in the first surface 71 are positioned on an outer side of the seal region 74.

As illustrated in FIG. 21, the reception portion 76 of the cap 70 receives the connector member 79 (equivalent to an example of the conductor) extending between the cap side surface 73 and the first surface 71. The connector member 79 is configured to have one end connected to the lead wire 51 of the heater 50 and the other end connected to a lead wire or terminal, which is not illustrated, of the battery portion 12 so as to conduct the lead wire 51 to the battery portion 12. In the illustrated example, the connector member 79 is configured to protrude from the hole of the reception portion 76, but is not limited thereto and may be configured such that the end of the connector member 79 is positioned in the reception portion 76. Note that, regarding the cap 70 illustrated in FIG. 20, illustration of the connector member 79 is omitted.

In cases where the cap 70 illustrated in FIGS. 20 and 21 is used in the cartridge 20, when the heater 50 is arranged on the liquid holding member 40, the lead wires 51 are brought into contact with or connected to the ends of the connector members 79 protruding from the reception portions 76 formed in the first surface 71. The connector members 79 protruding from the reception portions 76 formed in the cap side surface 73 are connected to the lead wire or terminal, which is not illustrated, of the battery portion 12. Thus, the heater 50 is conducted to the battery portion 12.

Similar to the cap 70 illustrated in FIGS. 2 to 19, the cap 70 illustrated in FIG. 20 also includes the reception portions 76 on an outer side of the seal region 74. Therefore, the leakage of the liquid in the tank 31 to the battery portion 12 side via the reception portions 76 can be prevented more reliably. Moreover, because the cap 70 illustrated in FIG. 20 includes the connector members 79 arranged in the reception portions 76, the heater 50 can be easily assembled to the cartridge 20 so as to be conducted to the battery portion 12. Furthermore, because the cap 70 illustrated in FIG. 20 is a plate-shaped body having a substantially semicircular shape, it is possible to increase the area of the air flow passage through which the internal space 62, which is formed by the cover member 60 and the housing 30, communicates with the space on the battery portion 12 side when the cap 70 is assembled to the cartridge 20. Accordingly, for example, when the air inlet port is provided on the upstream side (battery portion 12 side) of the cap 70, the air can be supplied to the internal space 62 from the upstream side of the cap 70. The cover member may not include the air inlet port. Note that the cap 70 illustrated in FIG. 20 does not include the protrusion portion 75 of the cap 70 illustrated in FIGS. 2 to 16, but may include the protrusion portion 75 in the seal region 74. Moreover, the reception portions 76 have a form of a hole penetrating through the cap side surface 73 and the first surface 71, but may instead have a form of a recess portion penetrating through the cap side surface 73 and the first surface 71.

Examples of the cap 70 in various forms have been described heretofore. The connector members 79 are an optional component of the cap 70 illustrated in FIGS. 17 to 21. Accordingly, when the cap 70 illustrated in FIGS. 17 to 21 does not include connector members 79, the lead wire of the heater 50 and the terminal of the battery portion 12 or the lead wire of the battery portion 12 are directly connected.

Second Embodiment

Next, an inhaler 10 according to the second embodiment is described. The inhaler 10 according to the second embodiment is the same as that of the first embodiment except for a cartridge 20. Therefore, only the cartridge 20 is described. FIG. 22 is an exploded perspective view of the cartridge 20 according to the second embodiment. FIG. 23 is a perspective view of the cartridge 20 according to the second embodiment in a state where a cap 70, a liquid holding member 40, and a heater 50 are assembled to a housing 30. As illustrated in FIG. 22, the cartridge 20 includes the housing 30, the liquid holding member 40, the heater 50, and the cap 70. Furthermore, the cartridge 20 according to the second embodiment includes retaining rings 90 for fixing the heater 50 and the liquid holding member 40 to the housing 30.

As illustrated in FIG. 22, the partition member 36 includes two pins 91 provided around a liquid supply port 32. The pins 91 are extended from the partition member 36 in the transverse direction of the cartridge 20. The liquid holding member 40 has insertion holes 41 into which the pins 91 are inserted. When the cartridge 20 is assembled, the cap 70 is attached to a tank 31 in the manner of sealing an opening 33. Next, the pins 91 are inserted into the insertion holes 41 of the liquid holding member 40, and the liquid holding member 40 is arranged on the cartridge 20 to cover the liquid supply port 32. The heater 50 is arranged on the liquid holding member 40 such that the pins 91 are arranged within the heater 50 having a U shape. At this time, lead wires 51 of the heater 50 are received on reception portions 76 of the cap 70. The member of the pins 91 is not particularly limited, but is preferably a heat-resistance member, e.g., ceramic.

Thereafter, the retaining rings 90 are fit to the pins 91. Furthermore, a cover member 60 closes a cutout portion 35 of a housing body 30a. Thus, the retaining rings 90 are held down by the cover member 60, preventing the retaining rings 90 from being removed from the pins 91. Thus, the heater 50 and the liquid holding member 40 are fixed to the housing 30.

As the cover member 60 used in the second embodiment, the cover member 60 illustrated in FIGS. 11 and 12 described in the first embodiment can be adopted. Moreover, as the cap 70 used in the second embodiment, the cap 70 illustrated in FIGS. 2 to 21 described in the first embodiment can be adopted. Moreover, the partition member 36 according to the second embodiment is described to include one liquid supply port 32, but is not limited thereto and can include any number of liquid supply ports 32.

Although the embodiments of the present invention are described above, the present invention is not limited to the aforementioned embodiments and various modifications may be made within the scope of the technical idea described in the claims, the specification, or the drawings. Note that, any shape or material not directly described in the specification or the drawings falls within the scope of the technical idea of the invention of the present application insofar as the shape or material provides an operation and effect of the invention of the present application.

REFERENCE SIGN LIST 10 inhaler
12 battery portion
20 cartridge
30 housing
31 tank
31a accommodation space
32 liquid supply port
33 opening
34 air outlet port
36 partition member
36c downstream-side opening edge
36d upstream-side opening edge
36e downstream-side end
36f upstream-side end
36g downstream portion
36h upstream portion
40 liquid holding member
50 heater
50b first end
50c second end
51 lead wire
60 cover member
61 air inlet port
62 air flow passage

The invention claimed is:

1. A cartridge for an inhaler, the cartridge comprising:
   a housing including an accommodation space capable of accommodating a liquid, an air flow passage, and a partition member partitioning the accommodation space and the air flow passage in a longitudinal direction; and
   a heater configured to be capable of heating the liquid and arranged in the air flow passage,
   wherein the partition member includes an opening opened in a transverse direction to bring the accommodation space into communication with the air flow passage,
   wherein the opening includes an upstream-side opening edge and a downstream-side opening edge,
   wherein the partition member includes an upstream-side end and a downstream-side end,
   wherein a distance between the upstream-side opening edge and the upstream-side end is smaller than a distance between the downstream-side opening edge and the downstream-side end,
   wherein the heater includes an upstream-side heater end and a downstream-side heater end, and
   wherein a distance between the upstream-side heater end and the upstream-side end is smaller than a distance between the downstream-side heater end and the downstream-side end.

2. The cartridge according to claim 1, wherein the partition member includes an upstream portion positioned between the upstream-side opening edge and the upstream-side end and a downstream portion positioned between the downstream-side opening edge and the downstream-side end, and
   wherein a longitudinal length of the downstream portion is longer than a longitudinal length of the upstream portion.

3. The cartridge according to claim 1, comprising:
   a liquid holding member arranged to cover the opening,
   wherein the liquid holding member is arranged between the opening and the heater.

4. The cartridge according to claim 1, wherein the housing includes an air outlet port communicating with the air flow passage.

5. The cartridge according to claim 1, comprising:
   an air inlet port provided at a position facing the heater and communicating with the air flow passage.

6. An inhaler comprising:
   the cartridge according to claim 1; and
   a battery portion configured to supply electric power to the heater of the cartridge.

* * * * *